(12) United States Patent
Detinis

(10) Patent No.: US 12,089,856 B2
(45) Date of Patent: *Sep. 17, 2024

(54) DRILLING DEVICES, SYSTEMS, AND METHODS

(71) Applicant: Mazor Robotics Ltd., Caesarea (IL)

(72) Inventor: Eitan Detinis, Shefayim (IL)

(73) Assignee: Mazor Robotics Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/160,252

(22) Filed: Jan. 26, 2023

(65) Prior Publication Data

US 2023/0172619 A1 Jun. 8, 2023

Related U.S. Application Data

(63) Continuation of application No. 17/163,951, filed on Feb. 1, 2021, now Pat. No. 11,564,700.

(51) Int. Cl.
*A61B 17/16* (2006.01)
*A61B 34/30* (2016.01)
(Continued)

(52) U.S. Cl.
CPC ...... *A61B 17/1644* (2013.01); *A61B 17/1626* (2013.01); *A61B 17/1628* (2013.01);
(Continued)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 8,105,366 B2 1/2012 Null et al.
10,105,234 B2 10/2018 Squires et al.
(Continued)

FOREIGN PATENT DOCUMENTS

CN 202044312 11/2011
CN 109770994 5/2019
(Continued)

OTHER PUBLICATIONS

International Search Report and Written Opinion for International (PCT) Patent Application No. PCT/IL2022/050132, dated May 10, 2022, 13 pages.

(Continued)

*Primary Examiner* — Eric S Gibson
(74) *Attorney, Agent, or Firm* — Sheridan Ross P.C.

(57) ABSTRACT

Devices, systems, and methods for drilling an anatomical element are provided. A drill bit may comprise a coaxial hollow shaft in communication with a plurality of apertures disposed on a surface of the drill bit. A fluid inlet may be in fluid communication with the coaxial hollow shaft via a selectively openable valve. The fluid inlet may be configured to receive pressurized fluid. When the valve is opened, the pressurized fluid may be released into the coaxial hollow shaft, and when at least one of the plurality of apertures is not blocked, the pressurized fluid may be released through the at least one aperture of the plurality of apertures.

19 Claims, 4 Drawing Sheets

(51) Int. Cl.
*A61B 90/00* (2016.01)
*A61B 17/00* (2006.01)
*A61M 39/22* (2006.01)

(52) U.S. Cl.
CPC .............. *A61B 34/30* (2016.02); *A61B 90/03* (2016.02); *A61B 2017/00123* (2013.01); *A61B 2090/064* (2016.02); *A61M 2039/226* (2013.01)

(58) Field of Classification Search
CPC ........... A61B 17/1622; A61B 17/1626; A61B 17/1628; A61B 17/1631; A61B 17/1633; A61B 17/1644; A61B 17/1646; A61B 17/1671; A61B 17/1695
See application file for complete search history.

(56) References Cited

U.S. PATENT DOCUMENTS

| | | | | |
|---|---|---|---|---|
| 10,448,933 B2 * | 10/2019 | Rioux | .................. | A61B 17/864 |
| 11,564,700 B2 * | 1/2023 | Detinis | .................. | A61B 34/30 |
| 2002/0031745 A1 * | 3/2002 | Kumar | ............... | A61B 17/1615 |
| | | | | 433/165 |
| 2006/0085005 A1 * | 4/2006 | Kenealy, III | ......... | A61C 8/0089 |
| | | | | 606/80 |
| 2009/0274996 A1 * | 11/2009 | Miller | .................... | A61C 1/084 |
| | | | | 433/165 |
| 2011/0137352 A1 * | 6/2011 | Biedermann | ...... | A61B 17/8635 |
| | | | | 606/305 |
| 2013/0190817 A1 * | 7/2013 | Bouduban | ........... | A61B 17/866 |
| | | | | 606/232 |
| 2018/0092662 A1 * | 4/2018 | Rioux | ................ | A61B 17/3423 |
| 2018/0093094 A1 * | 4/2018 | Wolf, II | ............... | A61N 1/0558 |
| 2022/0240951 A1 * | 8/2022 | Detinis | ............. | A61B 17/1644 |
| 2023/0172619 A1 * | 6/2023 | Detinis | .................. | A61B 34/30 |
| | | | | 606/80 |

FOREIGN PATENT DOCUMENTS

| | | | | |
|---|---|---|---|---|
| CN | 112914675 | | 6/2021 | |
| CN | 112914675 A | * | 6/2021 | ......... A61B 17/1615 |
| GB | 2438877 | | 12/2007 | |
| GB | 2438877 A | * | 12/2007 | ......... A61B 17/1626 |
| KR | 10-2014-0069431 | | 6/2014 | |
| WO | WO-0209598 A2 | * | 2/2002 | ......... A61B 17/1615 |
| WO | WO 02/054941 | | 7/2002 | |
| WO | WO 2007/141578 | | 12/2007 | |
| WO | WO-2007141578 A2 | * | 12/2007 | ......... A61B 17/1626 |
| WO | WO 2018/067525 | | 4/2018 | |
| WO | WO-2018067525 A1 | * | 4/2018 | ........... A61B 10/025 |
| WO | WO 2018/080402 | | 5/2018 | |
| WO | WO 2021/205397 | | 10/2021 | |
| WO | WO-2021205397 A1 | * | 10/2021 | ......... A61B 17/1615 |

OTHER PUBLICATIONS

Notice of Allowance for U.S. Appl. No. 17/163,951, dated Sep. 16, 2022, 8 pages.

* cited by examiner

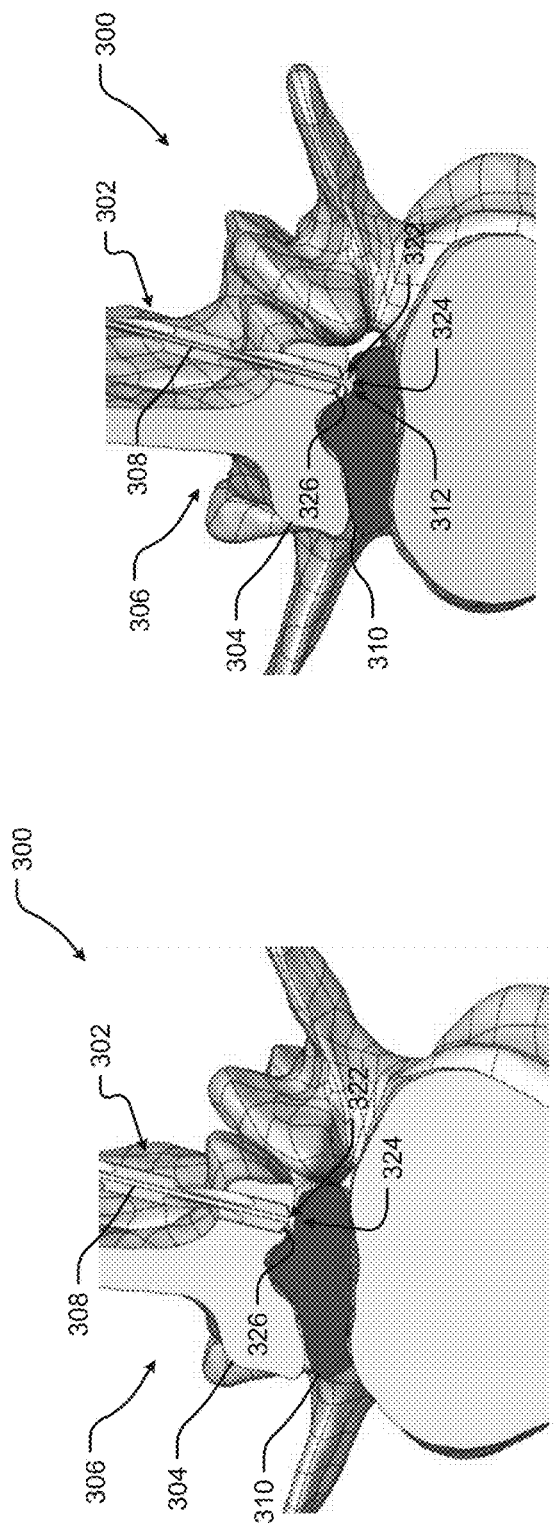
FIG. 3A
FIG. 3B
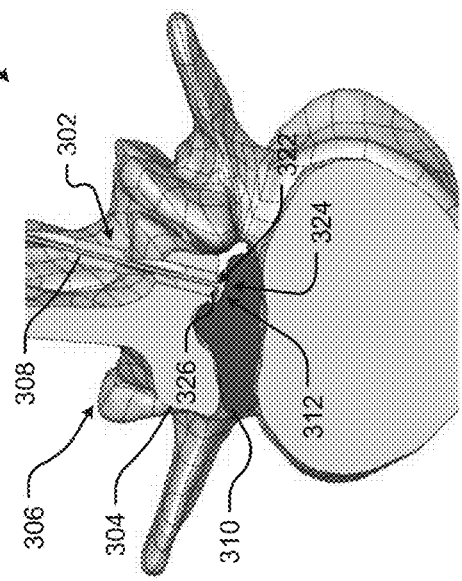
FIG. 3C

DRILLING DEVICES, SYSTEMS, AND METHODS

CROSS REFERENCE TO RELATED APPLICATIONS

This application is a continuation of U.S. patent application Ser. No. 17/163,951, filed on Feb. 1, 2021, and entitled "DRILLING DEVICES, SYSTEMS, AND METHODS," the entire disclosure of which is incorporated herein by reference in its entirety.

FIELD

The present technology generally relates to drill devices, and relates more particularly to drill bits for drilling an anatomical element.

BACKGROUND

Surgical robots may assist a surgeon or other medical provider in carrying out a surgical procedure, or may complete one or more surgical procedures autonomously. During such surgical procedures, surgical tools may be used on one or more anatomical elements. The tools may be oriented and operated by the surgical robot and/or the surgeon or other medical provider.

SUMMARY

Example aspects of the present disclosure include:

A device for drilling an anatomical element according to at least one embodiment of the present disclosure comprises a drill bit comprising a coaxial hollow shaft in communication with a plurality of apertures disposed on a surface of the drill bit, one aperture of the plurality of apertures disposed on a tip of the drill bit and one or more apertures of the plurality of apertures disposed at an angle to an axis of the coaxial hollow shaft; a fluid inlet in fluid communication with the coaxial hollow shaft via a selectively openable valve, the fluid inlet configured to receive pressurized fluid; and wherein when the valve is opened, the pressurized fluid is released into the coaxial hollow shaft, and when at least one of the plurality of apertures is not blocked, the pressurized fluid is released through the at least one aperture of the plurality of apertures.

Any of the aspects herein, further comprising: at least one processor; and a memory storing instructions for execution by the at least one processor that, when executed, cause the at least one processor to: cause the drill bit to rotate and advance, cause the valve to open, and monitor a pressure of the fluid via a pressure sensor in fluid communication with the coaxial hollow shaft.

Any of the aspects herein, wherein the memory stores additional instructions for execution by the at least one processor that, when executed, further cause the at least one processor to: receive sensor data from the pressure sensor; and compare the sensor data to a predetermined threshold.

Any of the aspects herein, wherein the memory stores additional instructions for execution by the at least one processor that, when executed, further cause the at least one processor to: cause the drill bit to advance when the pressure of the fluid is above the predetermined threshold.

Any of the aspects herein, wherein the memory stores additional instructions for execution by the at least one processor that, when executed, further cause the at least one processor to: open the valve once the drill bit has been activated for a predetermined period of time, the drill bit has reached a predetermined drilling depth, or a predetermined drilling time has passed.

Any of the aspects herein, further comprising: at least one processor; and a memory storing instructions for execution by the at least one processor that, when executed, cause the at least one processor to: cause the drill bit to rotate and advance, cause the valve to open, and monitor a flow rate of the fluid via a flow sensor in fluid communication with the coaxial hollow shaft.

Any of the aspects herein, wherein the memory stores additional instructions for execution by the at least one processor that, when executed, further cause the at least one processor to: receive sensor data from the flow sensor; and compare the sensor data to a predetermined threshold.

A device for drilling an anatomical element according to at least one embodiment of the present disclosure comprises a drill bit comprising a coaxial hollow shaft in communication with a plurality of apertures disposed on a surface of the drill bit, one aperture of the plurality of apertures disposed on a tip of the drill bit; at least one processor; and a memory storing instructions for execution by the at least one processor that, when executed, cause the at least one processor to: cause the drill bit to rotate, open a valve that releases pressurized fluid into the coaxial hollow shaft, and monitor a pressure of the fluid to detect release of the pressurized fluid through one or more of the plurality of apertures.

Any of the aspects herein, wherein the memory stores additional instructions for execution by the at least one processor that, when executed, further cause the at least one processor to: receive sensor data from a sensor configured to measure the pressure of the fluid; and identify a drop in the pressure of the fluid based on the sensor data.

Any of the aspects herein, wherein the memory stores additional instructions for execution by the at least one processor that, when executed, further cause the at least one processor to: cause the drill bit to advance until the drop in the pressure of the fluid is identified.

Any of the aspects herein, wherein the memory stores additional instructions for execution by the at least one processor that, when executed, further cause the at least one processor to: cause the drill bit to stop when the drop in the pressure of the fluid is identified.

Any of the aspects herein, wherein the plurality of apertures have a non-circular cross section.

A system for drilling an anatomical element according to at least one embodiment of the present disclosure comprises a drill bit configured to drill an anatomical element, the drill bit comprising a coaxial hollow shaft in communication with at least one aperture disposed on a surface of the drill bit; a fluid system in fluid communication with the coaxial hollow shaft, the fluid system configured to pressurize a fluid and to dispense the pressurized fluid into the coaxial hollow shaft; a motor operatively connected to the drill bit; a user interface for selectively operating the motor; at least one processor; and a memory storing instructions for execution by the at least one processor that, when executed, cause the at least one processor to: cause the motor to rotate the drill bit, cause the fluid system to pressurize the fluid and dispense the pressurized fluid into the coaxial hollow shaft, and monitor a pressure of the fluid to detect release of the pressurized fluid through the at least one aperture.

Any of the aspects herein, wherein the at least one aperture is coaxial with the hollow shaft.

Any of the aspects herein, wherein the at least one aperture is a plurality of apertures and one or more apertures of the plurality of apertures are not coaxial with the hollow shaft.

Any of the aspects herein, wherein the fluid is at least one of water or saline.

Any of the aspects herein, further comprising: a robotic arm configured to orient the drill bit.

Any of the aspects herein, wherein the fluid system is configured to dispense the pressurized fluid into the coaxial hollow shaft after a predetermined period of time after activation of the drill bit, at a predetermined drilling depth, or after a predetermined drilling time.

Any of the aspects herein, further comprising: a pressure sensor configured to monitor the pressure of the fluid, and wherein the motor is configured to stop upon detection of a pressure drop by the pressure sensor.

Any of the aspects herein, wherein an alert is generated and communicated via the user interface upon detection of the pressure drop by the pressure sensor.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 3A is a cross-section view of a drilling system according to at least one embodiment of the present disclosure;

FIG. 3B is a cross-section view of a drilling system according to at least one embodiment of the present disclosure;

FIG. 3C is a cross-section view of a drilling system according to at least one embodiment of the present disclosure.

DETAILED DESCRIPTION

Figure 1:
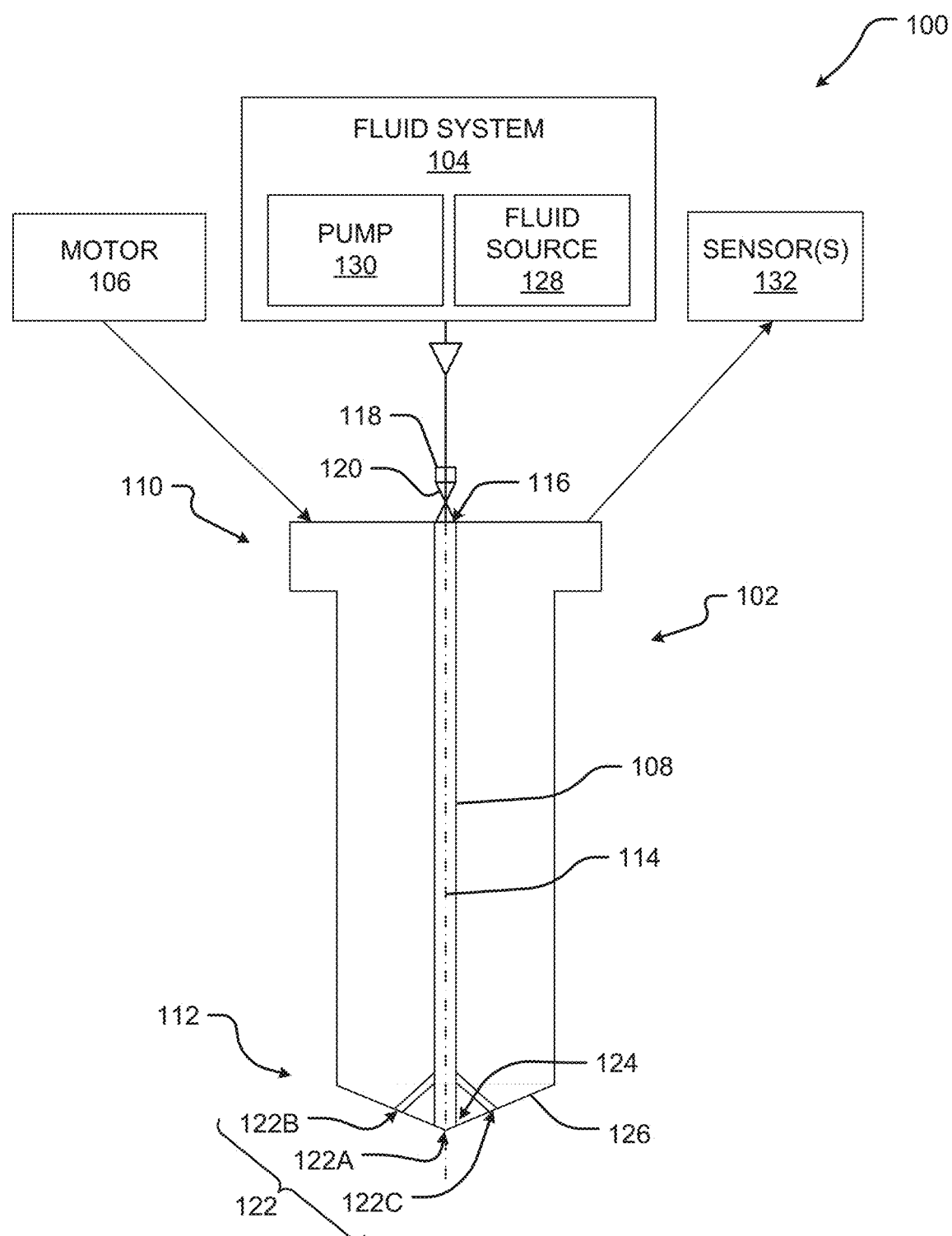
FIG. 1 is a schematic cross-section view of a drilling system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

During a surgical procedure, a drilling device such as a drill bit may be used to drill through bone, such as a vertebra. In some procedures such as decompression procedures, serious risk may be present while using a drill bit. For example, the drill bit may be used to drill through hard tissue (such as bone including a vertebra or skull) adjacent to sensitive soft tissue (such as dura matter, a spinal cord, brain tissue, etc.) that requires protection. In some decompression procedures, a hole is drilled through, for example, a lamina in preparation for a laminectomy or a laminotomy. As the drill bit penetrates through the lamina and if the drill bit is inserted too much further than intended, then the drill bit may penetrate through the ligamentum flavum and/or dura and possibly cause damage to a spinal region of a patient.

At least one embodiment is provided as a potential solution to the risk to the dura and/or ligamentum flavum during drilling of an initial hole of a lamina. According to embodiments of the present disclosure, two different measures are taken to prevent such damage: (1) sensing when the drill bit breaches the lamina into the spinal canal and (2) creating a protective barrier layer between the sharp drill tip and the soft tissue. In some embodiments, a method is provided that includes drilling the lamina using a hollow drill bit, configured such that water (or other fluid, such as viscous fluid for example) may pass through the drill's central hole and exit the drill bit near a tip thereof (and/or such that water or other fluid may pass through other peripheral holes extending from the central hole to an outer edge of the drill bit, and exit the drill bit through a side surface thereof). Before breaching the other side of the lamina, the water or other fluid is introduced under pressure (e.g., a reasonable pressure that will not cause harm to bodily tissue) within the hollow drill bit. Bone and/or other hard anatomical tissue prevents the fluid from escaping the hollow drill bit until the moment the drill bit breaches the cortical bone near the dura, at which point water exiting the drill bit through one or more holes therein splashes outside the lamina and pushes the soft tissue away from the drill's sharp edge. Further, real-time measurement of a fluid pressure and/or a flow rate can be used as a sensing method to determine when to stop advancing the drill bit (e.g., based on when a fluid pressure drop or a flow rate increase, even if temporary, is measured).

Embodiments of the present disclosure provide technical solutions to one or more of the problems of (1) preventing damage to sensitive anatomical matter, (2) sensing when a drill bit breaches an anatomical element, and (3) increasing patient safety during a surgical procedure.

Turning first to FIG. 1, a schematic drawing of a drilling system 100 and a cross-section view of a drill bit is shown. The drilling system 100 may be used drill any anatomical element, and may be particularly useful where the cutting or drilling may take place near any sensitive and/or soft tissue. In some embodiments, the drilling system 100 is used when hard tissue (such as bone) is cut or drilled adjacent to soft tissue. The drilling system 100 beneficially protects sensitive soft tissue from damage when adjacent hard tissue is being cut or drilled. The drilling system 100 includes a drill bit 102, a fluid system 104, a motor 106, and at least one sensor 132. Drilling systems according to other embodiments of the present disclosure may comprise more or fewer components (for example, a system may further include a user interface 310, a processor 304, or a memory 306, each shown in FIG. 3) than the drilling system 100.

The drill bit 102 comprises a shaft 108 extending from a first end 110 to a second end 112. The shaft 108 may be hollow and configured to receive a fluid. In other words, the shaft 108 may act as a fluid channel. In the illustrated embodiment, the shaft 108 is coaxial with an axis 114 that extends through a center of the drill bit 102. In other embodiments, all or a portion of the shaft 108 may not be coaxial with the axis 114. For example, all or a portion of the shaft 108 may be offset from the axis 114. In the illustrated embodiment, the shaft 108 is cylindrical in shape. In other embodiments, all or a portion of the shaft 108 may not be cylindrical. For example, all or a portion of the shaft 108 may be a spiral shape to increase a channel diameter without compromising a strength of the drill bit 102 or the drilling capabilities. Such increased channel diameter may allow for a lower pressure input to the drill bit 102. The shaft 108 may have an opening 116 at the first end 110. In the illustrated embodiment, the opening 116 is coaxial with the axis 114. In other embodiments, the opening 116 may not be coaxial with the axis 114 and may be disposed at any angle from the axis 114. In some embodiments, the opening 116 is in fluid communication with a fluid source 128 of the fluid system 104. The opening 116 may be in fluid communication with the fluid source 128 by a hose or a tube. In other embodiments, the opening 116 is in fluid communication with the fluid source 128 through a fluid inlet 118 and a valve 120. In the illustrated embodiment, the fluid inlet 118 and the valve 120 are coaxial with the axis 114. In other embodiments, the fluid inlet and/or the valve 120 are not coaxial with the axis 114. In such embodiments, each may be disposed at any angle from the axis 114.

The shaft 108 is also in fluid communication with at least one aperture 122 disposed on a surface 126 of the drill bit 102. In some embodiments, the at least one aperture 122 may have a circular cross-section. In other embodiments, the at least one aperture 122 may have a non-circular cross-section. In embodiments where the at least one aperture 122 comprises a plurality of apertures, each aperture of the plurality of apertures may have the same cross section, may have a different cross section, or some apertures of the plurality of apertures may have the same cross section while other apertures have a different cross section.

The shaft 108 may be in fluid communication with one aperture, two apertures, or more than two apertures. In the illustrated embodiment the at least one aperture 122 comprises a first aperture 122A, a second aperture 122B, and a third aperture 122C. The first aperture 122A may be coaxial with the axis 114 and open onto a tip 124 of the drill bit 102 at the second end 112. The second aperture 122B and the third aperture 122C may not be coaxial with the axis 114. In other words, the second aperture 122B and the third aperture 122C may be disposed at an angle relative to the axis 114 and may be referred to as peripheral apertures.

During use, pressurized fluid is moved from the fluid source 128 into the shaft 108 of the drill bit 102. The fluid may be a gas (e.g., oxygen, air, carbon dioxide, heliox) or a liquid (e.g., water, saline, or another irrigant). In embodiments that include the fluid inlet 118 and the valve 120, the fluid inlet 118 is configured to receive the pressurized fluid and when the valve 120 is opened, the pressurized fluid is released into the shaft 108. The fluid may initially fill the shaft 108 and/or any channels leading from the shaft 108 to any peripheral apertures 122. As will be described more fully below, as the drill bit 102 drills through an anatomical element (such as a bone), the at least one aperture 122 may be blocked by the anatomical element. When the drill bit 102 begins to emerge on a side of the anatomical element, one or more apertures may become unblocked by the anatomical element and therefore, fluid may be released through the one or more unblocked apertures. In other words, the fluid is released through any one or more apertures 122 that are not blocked.

The fluid may be pressurized and delivered by a pump 130 of the fluid system 104. The pump 130 may be any kind of pump 130 including a centrifugal pump or a positive displacement pump. The pump 130 may also be submersible inside the fluid source 128 or may be disposed outside of the fluid source 128. In some embodiments, the pump 130 may be driven by a motor. In other embodiments, the pump 130 may be a hand pump and may be manually operated.

The system 100 may also include a motor 106, configured to rotate the drill bit 102. The motor 106 may be an electric motor, a pneumatic motor, a hydraulic motor, or another type of motor. In some embodiments, the motor 106 comprises a gear motor. In other embodiments, the motor 106 comprises any type of motor including an AC brushless motor, a DC brushed motor, a DC brushless motor, a servo motor, or the like. The motor 106 may comprise (or be operably connected to) an electronic speed control configured to control a speed of rotation thereof.

The system 100 may also include at least one sensor 132 configured to monitor a pressure and/or a flow rate of the fluid. The sensor 132 may be in fluid communication with the shaft 108. In some embodiments, the sensor 132 may be positioned on or in the drill bit 102. In other embodiments, the sensor 132 may be positioned on or in the pump 130, the fluid source 128, the fluid inlet 118, or the valve 120. In yet other embodiments, the sensor may be positioned on any component of the drilling system 100 or the system 200, described in detail with respect to FIG. 2. The at least one sensor 132 may be any kind of sensor 132 for sensing the fluid pressure and/or the flow rate. The sensor 132 may include one or more or any combination of components that are electrical, mechanical, electro-mechanical, magnetic, electromagnetic, or the like. The sensor 132 may include one or more of a flow sensor, a barometer sensor, a manometer sensor, a pressure transducer, a strain gauge pressure transducer, a capacitance pressure transducer, a potentiometric pressure transducer, or the like. In embodiments where the sensor 132 includes at least a flow sensor, the flow sensor may be configured to measure the flow rate of the fluid (e.g., into the drill bit 102, through the drill bit 102) and may be configured to sense when the drill bit 102 breaches an anatomical element (e.g., by detecting a change in flow rate due to fluid flowing out of the drill bit 102). In some embodiments, the sensor 132 may include a memory for storing sensor data. In still other examples, the sensor 132 may output signals (e.g., sensor data) to one or more sources (e.g., a computing device 202, a processor 204, or a memory 206 shown in FIG. 2).

Figure 2:
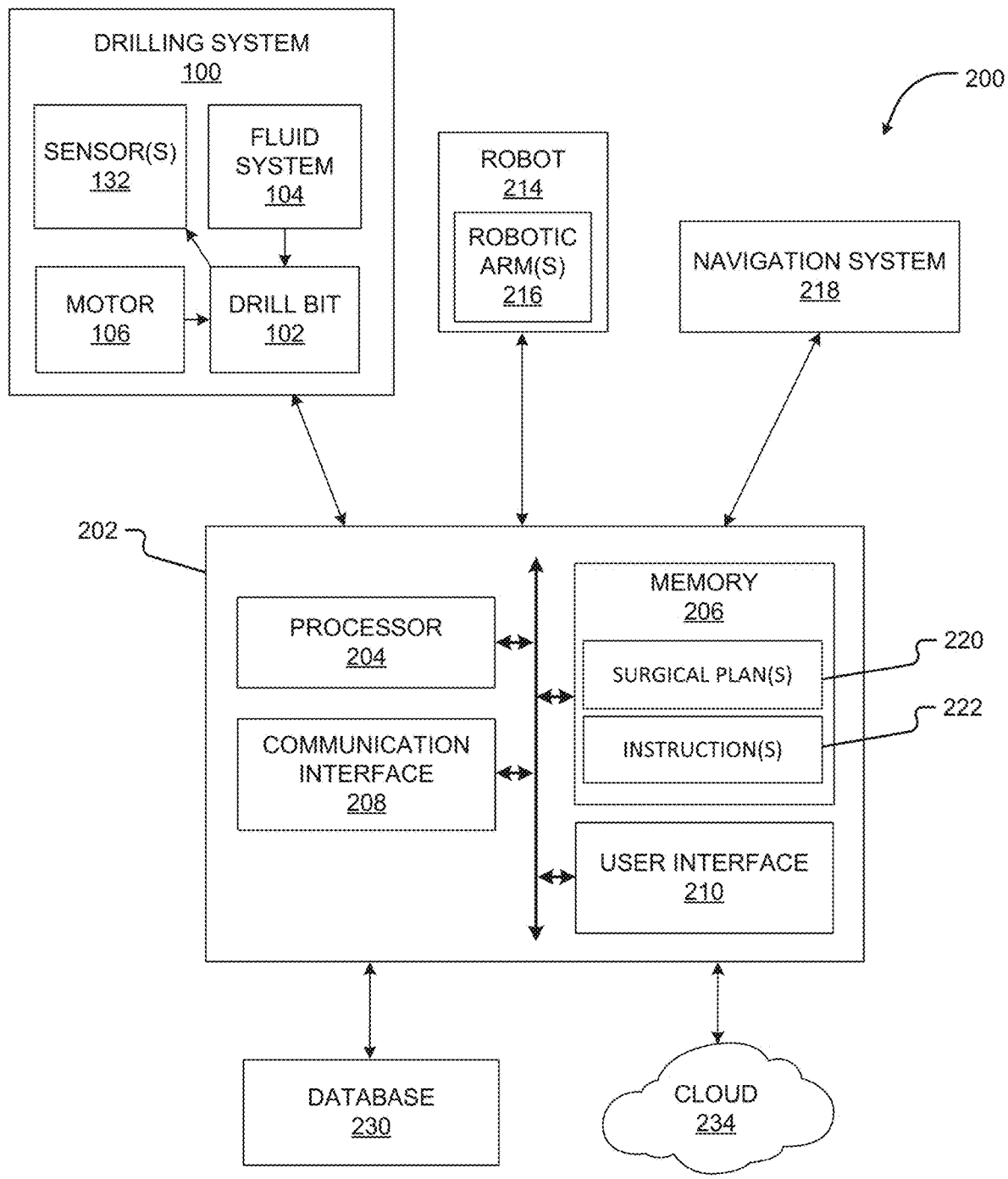
FIG. 2 is a block diagram of a system according to at least one embodiment of the present disclosure.

Turning to FIG. 2, a block diagram of a system 200 according to at least one embodiment of the present disclosure is shown. The system 200 may be used to monitor and control drilling of an anatomical element using a drill bit and to detect when the drill bit breaches a side of the anatomical element. The system 200 may also be used to carry out one or more other aspects of one or more of the methods disclosed herein.

The system 200 comprises the drilling system 100, described above with respect to FIG. 1, a computing device 202, a robot 214, a navigation system 218, a database 230, and/or a cloud or other network 234. The drilling system 100 may be operated automatically or partially automatically (e.g., with assistance and/or input from a surgeon or operator) by the system 200. Systems according to other embodiments of the present disclosure may comprise more or fewer components than the system 200. For example, the system 200 may not include the robot 214, the navigation system 218, one or more components of the computing device 202, the database 230, and/or the cloud 234.

The computing device 202 comprises a processor 204, a memory 206, a communication interface 208, and a user interface 210. Computing devices according to other embodiments of the present disclosure may comprise more or fewer components than the computing device 202.

The processor 204 of the computing device 202 may be any processor described herein or any similar processor. The processor 204 may be configured to execute instructions stored in the memory 206, which instructions may cause the processor 204 to carry out one or more computing steps utilizing or based on data received from the robot 214, the navigation system 218, the database 230, and/or the cloud 234.

The memory 206 may be or comprise RAM, DRAM, SDRAM, other solid-state memory, any memory described herein, or any other tangible, non-transitory memory for storing computer-readable data and/or instructions. The memory 206 may store information or data useful for completing, for example, any step of the method 400 described herein, or of any other methods. The memory 206 may store, for example, one or more surgical plans 220 and/or one or more sets of instructions 222. Such instructions 222 may, in some embodiments, be organized into one or more applications, modules, packages, layers, or engines. The instructions 222 may cause the processor 204 to manipulate data stored in the memory 206 and/or received from or via the drilling system 100, the robot 214, the database 230, and/or the cloud 234.

The computing device 202 may also comprise a communication interface 208. The communication interface 208 may be used for receiving data (such as sensor data) or other information from an external source (such as the robot 214, the navigation system 218, the database 230, the cloud 234, and/or any other system or component not part of the system 200), and/or for transmitting instructions or other information to an external system or device (e.g., another computing device 202, the robot 214, the navigation system 218, the database 230, the cloud 234, and/or any other system or component not part of the system 200). The communication interface 208 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 208 may be useful for enabling the device 202 to communicate with one or more other processors 204 or computing devices 202, whether to reduce the time needed to accomplish a computing-intensive task or for any other reason.

The computing device 202 may also comprise one or more user interfaces 210. The user interface 210 may be or comprise a keyboard, mouse, trackball, monitor, television, screen, touchscreen, and/or any other device for receiving information from a user (such as a predetermined pressure and/or flow rate threshold, a drilling depth, a period of time of drilling, etc.) and/or for providing information to a user. The user interface 210 may be used, for example, to receive a user selection or other user input regarding any step of any method described herein. Notwithstanding the foregoing, any required input for any step of any method described herein may be generated automatically by the system 200 (e.g., by the processor 204 or another component of the system 200) or received by the system 200 from a source external to the system 200. In some embodiments, the user interface 210 may be useful to allow a surgeon or other user to modify instructions to be executed by the processor 204 according to one or more embodiments of the present disclosure, and/or to modify or adjust a setting of other information displayed on the user interface 210 or corresponding thereto.

Although the user interface 210 is shown as part of the computing device 202, in some embodiments, the computing device 202 may utilize a user interface 210 that is housed separately from one or more remaining components of the computing device 202. In some embodiments, the user interface 210 may be located proximate one or more other components of the computing device 202, while in other embodiments, the user interface 210 may be located remotely from one or more other components of the computer device 202.

The navigation system 218 may provide navigation for a surgeon and/or a surgical robot during an operation. The navigation system 218 may be any now-known or future-developed navigation system, including, for example, the Medtronic StealthStation™ S8 surgical navigation system or any successor thereof. The navigation system 218 may include one or more cameras or other sensor(s) for tracking one or more reference markers, navigated trackers, or other objects within the operating room or other room in which some or all of the system 200 is located. The one or more cameras may be optical cameras, infrared cameras, or other cameras. In some embodiments, the navigation system may comprise one or more electromagnetic sensors. In various embodiments, the navigation system 218 may be used to track a position and orientation (i.e., pose) of the robot 214 and/or robotic arm 216, and/or one or more surgical tools such as the drill bit 102 (or, more particularly, to track a pose of a navigated tracker attached, directly or indirectly, in fixed relation to one or more of the foregoing). The navigation system 218 may include a display for displaying one or more images from an external source (e.g., the computing device 202, or other source) or for displaying an image and/or video stream from the one or more cameras or other sensors of the navigation system 218. In some embodiments, the system 200 can operate without the use of the navigation system 218. The navigation system 218 may be configured to provide guidance to a surgeon or other user of the system 200 or a component thereof, to the robot 214, or to any other element of the system 200 regarding, for example, a pose of one or more anatomical elements and/or whether or not a drill bit such as the drill bit 102 is in the proper trajectory, and/or how to move the drill bit 102 into the proper trajectory to carry out a surgical task according to a preoperative or other surgical plan such as the surgical plan 220.

The robot 214 may be any surgical robot or surgical robotic system. The robot 214 may be or comprise, for example, the Mazor X™ Stealth Edition robotic guidance system. The robot 214 may be configured to position a drill bit such as the drill bit 102 at one or more precise position(s) and orientation(s), and/or to return the drill bit 102 to the same position(s) and orientation(s) at a later point in time. The robot 214 may additionally or alternatively be configured to manipulate a surgical tool such as the drill bit 102 (whether based on guidance from the navigation system 218 or not) to accomplish or to assist with a surgical task. In some embodiments, the robot 214 may be configured to hold and/or manipulate an anatomical element during or in connection with a surgical procedure. The robot 214 may comprise one or more robotic arms 216. In some embodiments, the robotic arm 216 may comprise a first robotic arm and a second robotic arm, though the robot 214 may comprise more than two robotic arms. In some embodiments, one or more of the robotic arms 216 may be used to hold and/or maneuver the drill bit 102.

The robot 214, together with the robotic arm 216, may have, for example, one, two, three, four, five, six, seven, or more degrees of freedom. Further, the robotic arm 216 may be positioned or positionable in any pose, plane, and/or focal point. The pose includes a position and an orientation. As a result, the drill bit 102, a surgical tool, or other object held by the robot 214 (or, more specifically, by the robotic arm 216) may be precisely positionable in one or more needed and specific positions and orientations.

The robotic arm(s) 216 may comprise one or more sensors that enable the processor 204 (or a processor of the robot 214) to determine a precise pose in space of the robotic arm (as well as any object or element held by or secured to the robotic arm).

In some embodiments, reference markers (i.e., navigation markers) may be placed on the robot 214 (including, e.g., on the robotic arm 216), or any other object in the surgical space. The reference markers may be tracked by the navigation system 218, and the results of the tracking may be used by the robot 214 and/or by an operator of the system 200 or any component thereof. In some embodiments, the navigation system 218 can be used to track other components of the system and the system can operate without the use of the robot 214 (e.g., with the surgeon manually manipulating the drill bit 102 and/or one or more surgical tools, based on information and/or instructions generated by the navigation system 218, for example).

The system 200 or similar systems may be used, for example, to carry out one or more aspects of the method 400 described herein. The system 200 or similar systems may also be used for other purposes.

Turning to FIGS. 3A-3C, a drill bit 302 of a drilling system 300 in a first position, a second position, and a third position respectively are shown to illustrate an example use of the drilling system 300. The drilling system 300 may be the same as or similar to the drill system 100 described above with respect to FIG. 1, and the drill bit 302 may be the same as or similar to the drill bit 102 also described above with respect to FIG. 1. As previously described, the drilling system 300 may be used drill any anatomical element and may be particularly useful where the cutting or drilling may take place near any sensitive and/or soft tissue. In some embodiments, the drilling system 300 is used when hard tissue (such as bone) is cut or drilled adjacent to soft tissue. The drilling system 300 beneficially protects sensitive soft tissue from damage when adjacent hard tissue is being cut or drilled.

As shown in FIG. 3A, the drill bit 302 is rotated and advanced through a lamina 304 of a vertebra 306. Though a vertebra 306 is shown for illustrative purposes, the drill bit 302 may drill through any anatomical element, particularly any hard tissue anatomical element. For example, in other embodiments, the drill bit 302 may drill or cut through a skull in which it is desirable to protect brain tissue adjacent to the skull. The drill bit 302 may be rotated by a motor such as the motor 106. As the drill bit 302 penetrates through the lamina 304, the drill bit 302 is exposed to anatomical matter 310 that is sensitive to tearing or damage (such as the dura, spinal cord, brain tissue, and/or other sensitive tissue) by the drill bit 302.

As shown in FIGS. 3B and 3C, pressurized fluid may be delivered to a hollow shaft 308 of the drill bit 302 by a fluid system such as the fluid system 104 and released through an aperture 322 of the drill bit 302 when the drill bit 302 penetrates through the lamina 304. More specifically, FIG. 3B illustrates when a tip 324 of the drill bit 302 initially breaks through the lamina 304 and the fluid exiting from the aperture 322 protects the anatomical matter 310. FIG. 3C illustrates when the pressurized fluid pushes the anatomical matter 310 (e.g., the dura) away from the tip 326 of the drill bit 302 to create space for the drill bit 302 to complete drilling the hole. As illustrated, the pressurized fluid may form a barrier 312 between the tip 324 of the drill bit 302 and the anatomical matter 310 to prevent contact between the drill bit 302 and the anatomical matter 310, which contact could damage the anatomical matter 310. The pressurized fluid may, in some instances, push the anatomical matter 310 away from the drill bit 302, as shown in FIG. 3C.

In some embodiments, the aperture 322 is disposed at the tip 324 of the drill bit 302 and fluid flowing from the aperture 322 forms the barrier 312 as soon as the tip 324 penetrates the lamina 304. In other embodiments, a plurality of apertures may be disposed on a surface 326 of the drill bit 302.

In instances where a different portion of the drill bit 302 (e.g., a portion of the drill bit 302 that is not the tip 324 such as a circumference of the drill bit 302) penetrates the lamina 304 first, whether due to an angle of drilling or otherwise, fluid may flow from the aperture first exposed (and no longer blocked by the lamina 304) to form the barrier 312. In other words, fluid may flow from the aperture that first penetrates the lamina 304 to form the barrier 312.

As described in more detail below, the pressurized fluid may be delivered prior to the drill bit 302 penetrating the lamina 304 (or any hard tissue) so as to form the barrier 312 as soon as the drill bit 302 penetrates through the lamina 304. Further, a pressure and/or a flow rate of the fluid may be monitored to detect a change in fluid pressure and/or flow rate, which may indicate penetration of the lamina 304. Once a drop in fluid pressure and/or an increase in the flow rate is detected, the drill bit 302 may be advanced a predetermined additional distance into the lamina or other tissue to fully drill out the hole, before being retracted. During such advancement and at least an initial period of the subsequent retraction, pressurized fluid continues to emanate from the one or more apertures in the drill bit 302 to prevent contact between the drill bit 302 and the anatomical matter 310 such as the dura (or other sensitive anatomical tissue).

Figure 4:
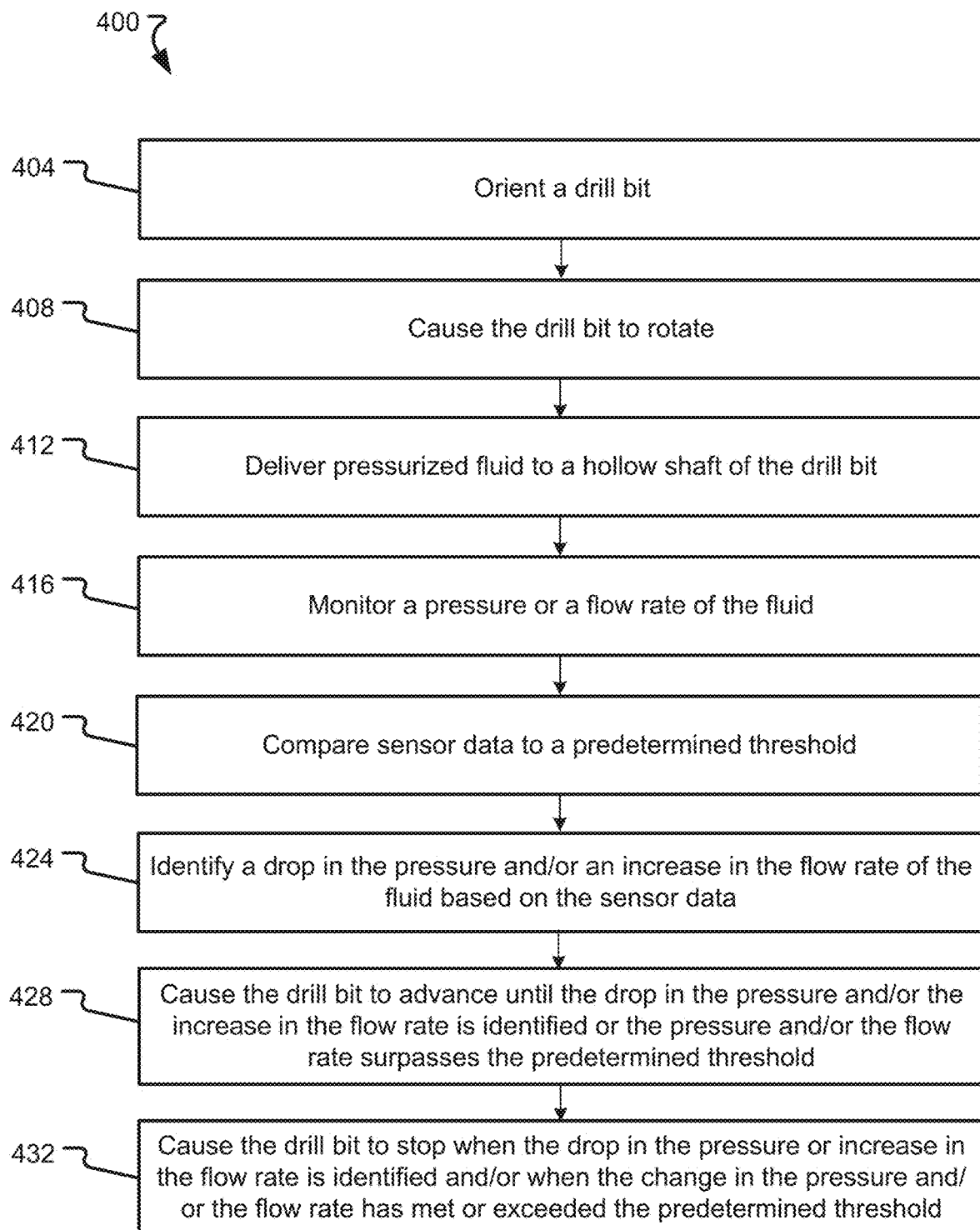
FIG. 4 is a flowchart according to at least one embodiment of the present disclosure.

FIG. 4 depicts a method 400 that may be used, for example, for drilling an anatomical element during a surgical procedure. In some embodiments, the anatomical element may be a vertebra and the method 400 may be used to prepare the lamina for a decompression procedure such as a laminectomy or a laminotomy. In other embodiments, the anatomical element may be any hard tissue. The method 400 may also be used to drill any hard tissue adjacent to sensitive soft tissue where it is desirable to protect or prevent damage to the sensitive soft tissue.

The method 400 (and/or one or more steps thereof) may be carried out or otherwise performed, for example, by at least one processor. The at least one processor may be the same as or similar to the processor(s) 204 of the computing device 202 described above. The at least one processor may be part of a robot (such as a robot 214) or part of a navigation system (such as a navigation system 218). A processor other than any processor described herein may also be used to execute the method 400. The at least one processor may perform the method 400 by executing instructions stored in a memory such as the memory 206. The instructions may correspond to one or more steps of the method 400 described below.

The method 400 comprises orienting a drill bit (step 404). The drill bit may be the same as or similar to the drill bit 102, 302. The drill bit may be oriented at an anatomical element. In some embodiments, the anatomical element is a vertebra. In other embodiments, the anatomical element may be any hard tissue such as bone. In some embodiments, a robotic arm such as the robotic arm 216 may automatically orient the drill bit. Alternatively, a surgeon or user may instruct the robotic arm to orient the drill bit. In other embodiments, the surgeon or a user may manually orient the drill bit.

In some embodiments, the robotic arm may orient the drill bit along a predetermined trajectory based on a surgical plan such as the surgical plan 220. In at least one of the embodiments, instructions such as the instructions 222 may be generated based on the surgical plan and transmitted to the robotic arm to cause the robotic arm to orient the drill bit. In other embodiments, the robotic arm may orient the drill bit based on input (e.g., using one or more coordinates, pose information, position information, or orientation information) from a surgeon or a user (which may be received from, for example, a user interface such as the user interface 210).

The method 400 also comprises causing the drill bit to rotate (step 408). A motor such as the motor 106 may rotate the drill bit. In some embodiments, a processor such as the processor 204 may automatically control the motor to cause the motor to rotate the drill bit. In other embodiments, the motor may rotate the drill bit based on input from the surgeon or the user (which may be received from, for example, the user interface). For example, a surgeon or other user may depress a trigger or otherwise activate the motor 106.

The step 408 may also comprise causing the drill bit to advance. The drill bit may be advanced by the robotic arm in some embodiments. Alternatively, a surgeon or user may instruct the robotic arm to advance the drill bit. In other embodiments, the surgeon or a user may manually advance the drill bit.

The drill bit be may be rotated and advanced for a predetermined period of time or a predetermined distance. A navigation system such as the navigation system 218 may be used to provide an indication of a drilling depth of the drill bit. The predetermined period of time or predetermined distance may be based on a surgical plan such as the surgical plan 220 or may be received as input from a surgeon or user via a user interface such as the user interface 210. Alternatively, a surgeon or user may monitor the drill bit (whether by imaging, measuring a depth of penetration, or otherwise) and advance the drill bit accordingly.

The method 400 also comprises delivering pressurized fluid to a shaft such as the shaft 108 of the drill bit (step 412). In some embodiments, the drill bit may be in fluid communication with a valve such as the valve 120, which is in fluid communication with a fluid inlet such as the fluid inlet 118. The fluid inlet may be configured to receive the pressurized fluid and the valve may control delivery of the pressurized fluid to the shaft. In some embodiments, the step 412 may include opening the valve to release the pressurized fluid into the shaft. After the fluid is delivered to the shaft, the fluid is released through at least one aperture (such as the at least one aperture 122, 322 disposed on a surface such as the surface 126, 226 of the drill bit) when the at least one aperture transitions to an unblocked state.

In some embodiments, fluid may be delivered to the shaft—whether by delivering the pressurized fluid directly to the shaft and/or by supplying pressurized fluid to the fluid inlet and opening the valve—once the drill bit has been activated for a predetermined period of time, the drill bit has reached a predetermined drilling depth, and/or a predetermined drilling time has passed. In other words, the drill bit may drill through a portion of the anatomical element before delivering pressurized fluid to the shaft. The predetermined period of time, the predetermined drilling length, and/or the predetermined drilling time may be based on a surgical plan such as the surgical plan 220. In other embodiments the fluid may be delivered to the shaft based on input received from a surgeon or a user via a user interface such as the user interface 210. In alternative embodiments, the fluid may be delivered to the shaft continuously throughout the drilling process.

The method 400 also comprises monitoring a pressure and/or a flow rate of the fluid (step 416). The step 416 may also include receiving sensor data from a sensor such as the sensor 132. The sensor may be any sensor configured to sense the pressure of the fluid (e.g., a pressure sensor) or configured to measure a flow rate of the fluid (e.g., a flow sensor or flow meter). In some embodiments, the sensor may continuously transmit sensor data to the processor, which may monitor the pressure and/or the flow rate. In other embodiments, the sensor may transmit sensor data to the processor at certain intervals (whether time intervals, depth intervals, or the like). The sensor data may be automatically monitored by the processor and/or may, in some instances, be displayed on a user interface such as the user interface 210 where a surgeon or a user may manually monitor the pressure and/or the flow rate.

The sensor may be in fluid communication with the shaft. In some embodiments, the sensor may be positioned on the drill bit. In other embodiments, the sensor may be positioned on the pump, the fluid source, the fluid inlet, or the valve. In yet other embodiments, the sensor may be positioned on any component of a drilling system such as the drilling system 100 or a system such as the system 200.

The method 400 also comprises comparing the sensor data to a predetermined threshold (step 420). The predetermined threshold may be obtained from a surgical plan such as the surgical plan 220. In other embodiments, the predetermined threshold may be received from a surgeon or a user via the user interface. In some embodiments, the predetermined threshold may be obtained pre-operatively or intra-operatively by measuring a pressure and/or a flow rate of the pressurized fluid when the pressurized fluid is delivered to the shaft (whether by opening the valve or directly delivering the pressurized fluid to the shaft) and the apertures of the drill bit are blocked (by bone, an obstruction, or otherwise). In some embodiments, the predetermined threshold may be a relative threshold rather than an absolute threshold. In other words, the predetermined threshold may be a 5% pressure drop, such that once the pressure drops and/or the flow rate increases by 5%, the predetermined threshold has been met.

The method 400 also comprises identifying a drop in the pressure and/or increase in the flow rate of the fluid based on the sensor data (step 424). The drop in the pressure and/or increase in the flow rate of the fluid may be identified by comparing the pressure and/or the flow rate of the fluid to the predetermined threshold executed in step 420. When the pressure and/or the flow rate of the fluid meets or surpasses the predetermined threshold (in an upward or downward direction, as appropriate), then an assumption can be made, based on the drop in pressure and/or increase in flow rate, that the drill bit has breached the bone or other hard tissue being drilled. In other embodiments, the drop in the pressure and/or increase in the flow rate may be identified by a surgeon or a user viewing the pressure and/or the flow rate on the user interface and identifying the drop in the pressure and/or increase in the flow rate. The surgeon or the user may then input the drop in the pressure and/or increase in the flow rate via the user interface.

The drop in the pressure and/or increase in the flow rate of the fluid indicates when the pressurized fluid is released through one or more apertures of the drill bit. More specifically, as the drill bit drills through an anatomical element such as a bone, the apertures are blocked by the bone and thus, fluid cannot be released through the apertures. When the drill bit penetrates through the anatomical element and at least one aperture is exposed to anatomical matter (e.g., dura, spinal cord, tissue, brain tissue) that is less hard than the bone, then the fluid is released through the at least one aperture and the pressure of the fluid will decrease and the flow rate of the fluid will increase. Either or both of these changes, when detected, indicate that the drill bit is no longer drilling through the bone. It will be appreciated that while the drill bit is drilling through the anatomical element (such as bone), some fluid may leak or be released from the at least one aperture. Such leak or release may not be significant enough to drop the pressure of the fluid to the predetermined threshold. Further, the predetermined threshold may account for such leaks.

The method 400 also comprises causing the drill bit to advance until the drop in the pressure and/or increase in the flow rate is identified or the pressure and/or the flow rate surpasses (in an upward or downward direction, as appropriate) the predetermined threshold (step 428). In some embodiments, the processor may generate and transmit instructions such as the instructions 222 to the motor and/or to the robotic arm to cause the motor to continue to rotate the drill bit and/or to cause the robotic arm to continue to advance the drill bit. In other embodiments, the processor may generate and communicate instructions to a surgeon or a user (e.g., via the user interface) to instruct the surgeon or the user to continue advancing the drill bit and/or continue operating the motor to rotate the drill bit. In yet other embodiments, the processor may generate and transmit instructions to the robotic arm and/or the motor and generate and communicate instructions to the surgeon or user. For example, the processor may generate and transmit instructions to the motor to cause the motor to rotate the drill bit and may generate and communicate instructions to a surgeon or a user to advance the drill bit.

The method 400 also comprises causing the drill bit to stop when the drop in pressure and/or increase in flow rate is identified, and/or when the change in pressure and/or flow rate of the fluid has met or exceeded the predetermined threshold (step 432). In some embodiments, the processor may generate and transmit instructions such as the instructions 222 to the motor and/or to the robotic arm to cause the motor to stop rotating the drill bit and/or to cause the robotic arm to stop advancing the drill bit. In other embodiments, the processor may generate and communicate instructions to a surgeon or a user (e.g., via the user interface) to instruct the surgeon or the user to stop advancing the drill bit and/or to stop operating the motor. In yet other embodiments, the processor may generate and transmit instructions to the robotic arm and/or the motor and generate and communicate instructions to the surgeon or user. For example, the processor may generate and transmit instructions to the motor to cause the motor to stop rotation of the drill bit and may generate and communicate instructions to a surgeon or a user to stop advancement of the drill bit.

The step 432 may also comprise retracting the drill bit. In some embodiments, the processor may generate and transmit instructions to the robotic arm to cause the robotic arm to retract the drill bit. In other embodiments, the processor may generate and communicate instructions to a surgeon or a user (e.g., via the user interface) to instruct the surgeon or the user to retract the drill bit. In some embodiments, the pressurized fluid is continuously delivered to the shaft during an entire period of time of the retraction of the drill bit. In other embodiments, the pressurized fluid is delivered to the shaft for a portion of the period of time of the retraction of the drill bit. For example, the pressurized fluid may be delivered to the shaft until the tip of the drill bit is inside of the anatomical element (such as a bone). This ensures that the barrier is in place to protect the sensitive anatomical matter until the drill bit is no longer at risk of contacting the sensitive anatomical matter.

The present disclosure encompasses embodiments of the method 400 that comprise more or fewer steps than those described above, and/or one or more steps that are different than the steps described above.

As noted above, the present disclosure encompasses methods with fewer than all of the steps identified FIG. 4 (and the corresponding description of the method 400), as well as methods that include additional steps beyond those identified in FIG. 4 (and the corresponding description of the method 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for drilling an anatomical element comprising:
   a drill bit comprising a coaxial hollow shaft in communication with at least one aperture disposed on a surface of the drill bit; and
   a fluid inlet in fluid communication with the coaxial hollow shaft via a selectively openable valve, the fluid inlet configured to receive pressurized fluid,
   wherein when the selectively openable valve is opened, the pressurized fluid is released into the coaxial hollow shaft and through the at least one aperture.

2. The device of claim 1, further comprising:
   at least one processor; and
   a memory storing instructions for execution by the at least one processor that, when executed, cause the at least one processor to:
   cause the drill bit to rotate and advance,
   cause the selectively openable valve to open, and
   monitor a pressure of the pressurized fluid via a pressure sensor in fluid communication with the coaxial hollow shaft.

3. The device of claim 2, wherein the memory stores additional instructions for execution by the at least one processor that, when executed, further cause the at least one processor to:
   receive sensor data from the pressure sensor, and
   compare the sensor data to a predetermined threshold.

4. The device of claim 3, wherein the memory stores additional instructions for execution by the at least one processor that, when executed, further cause the at least one processor to:
cause the drill bit to advance when the pressure of the pressurized fluid is above the predetermined threshold.

5. The device of claim 2, wherein the memory stores additional instructions for execution by the at least one processor that, when executed, further cause the at least one processor to:
open the selectively openable valve once the drill bit has been activated for a predetermined period of time, the drill bit has reached a predetermined drilling depth, or a predetermined drilling time has passed.

6. The device of claim 1, wherein the at least one aperture comprises a plurality of apertures, and wherein the pressurized fluid is released into the coaxial hollow shaft when at least one of the plurality of apertures is unblocked.

7. The device of claim 1, wherein a first aperture of the at least one aperture is disposed on a tip of the drill bit and a second aperture of the at least one aperture is disposed at an angle to an axis of the coaxial hollow shaft.

8. A device for drilling an anatomical element comprising:
a drill bit comprising a coaxial hollow shaft in communication with at least one aperture disposed on a surface of the drill bit;
at least one processor; and
a memory storing instructions for execution by the at least one processor that, when executed, cause the at least one processor to:
cause the drill bit to rotate,
open a valve that releases pressurized fluid into the coaxial hollow shaft, and
monitor a pressure of the pressurized fluid to detect release of the pressurized fluid through the at least one aperture.

9. The device of claim 8, wherein the memory stores additional instructions for execution by the at least one processor that, when executed, further cause the at least one processor to:
receive sensor data from a sensor configured to measure the pressure of the pressurized fluid, and
identify a drop in the pressure of the pressurized fluid based on the sensor data.

10. The device of claim 8, wherein the at least one aperture is coaxial with the coaxial hollow shaft.

11. The device of claim 8, wherein the at least one aperture is a plurality of apertures and one or more apertures of the plurality of apertures is disposed at an angle to an axis of the coaxial hollow shaft.

12. The device of claim 8, wherein the at least one aperture has a non-circular cross section.

13. A system for drilling an anatomical element comprising:
a drill bit configured to drill an anatomical element, the drill bit comprising a coaxial hollow shaft in communication with at least one aperture disposed on a surface of the drill bit;
a fluid system in fluid communication with the coaxial hollow shaft, the fluid system configured to pressurize a fluid and to dispense the pressurized fluid into the coaxial hollow shaft;
a motor operatively connected to the drill bit;
a user interface for selectively operating the motor;
at least one processor; and
a memory storing instructions for execution by the at least one processor that, when executed, cause the at least one processor to:
cause the motor to rotate the drill bit,
cause the fluid system to pressurize the fluid and dispense the pressurized fluid into the coaxial hollow shaft, and
monitor a pressure of the pressurized fluid to detect release of the pressurized fluid through the at least one aperture.

14. The system of claim 13, wherein the at least one aperture is coaxial with the coaxial hollow shaft.

15. The system of claim 13, wherein the at least one aperture is a plurality of apertures and one or more apertures of the plurality of apertures is disposed at an angle to an axis of the coaxial hollow shaft.

16. The system of claim 13, wherein the fluid is at least one of water or saline.

17. The system of claim 13, wherein the fluid system is configured to dispense the pressurized fluid into the coaxial hollow shaft after a predetermined period of time after activation of the drill bit, at a predetermined drilling depth, or after a predetermined drilling time.

18. The system of claim 13, further comprising:
a pressure sensor configured to monitor the pressure of the pressurized fluid, and wherein the motor is configured to stop upon detection of a pressure drop by the pressure sensor.

19. The system of claim 18, wherein an alert is generated and communicated via the user interface upon detection of the pressure drop by the pressure sensor.

* * * * *